(12) United States Patent
Stephan et al.

(10) Patent No.: US 8,168,113 B2
(45) Date of Patent: May 1, 2012

(54) METHOD FOR THE PRODUCTION OF A CERAMIC MOLDED PART

(75) Inventors: Marc Stephan, Lörrach (DE); Norbert Thiel, Bad Säckingen (DE); Enno Bojemüller, Bad Säckingen (DE)

(73) Assignee: Vita Zahnfabrik H. Rauter GmbH & Co. KG, Sackingen (DE)

( * ) Notice: Subject to any disclaimer, the term of this patent is extended or adjusted under 35 U.S.C. 154(b) by 520 days.

(21) Appl. No.: 12/310,998

(22) PCT Filed: Oct. 4, 2007

(86) PCT No.: PCT/EP2007/060546
§ 371 (c)(1),
(2), (4) Date: Mar. 16, 2009

(87) PCT Pub. No.: WO2008/040780
PCT Pub. Date: Apr. 10, 2008

(65) Prior Publication Data
US 2009/0311650 A1    Dec. 17, 2009

(30) Foreign Application Priority Data

Oct. 5, 2006    (EP) .................................... 06020897

(51) Int. Cl.
*B29C 43/00* (2006.01)
*B32B 3/26* (2006.01)

(52) U.S. Cl. ............. 264/517; 264/16; 264/17; 264/18; 264/645; 264/667; 264/670; 264/681; 264/500; 264/510; 264/345; 428/307.3; 428/307.7; 428/314.2; 428/688; 428/702; 433/213; 501/80; 523/115

(58) Field of Classification Search ........................ None
See application file for complete search history.

(56) References Cited

U.S. PATENT DOCUMENTS

| 2,463,551 | A | 3/1949 | Myerson et al. |
| 4,155,964 | A | 5/1979 | Aronow |
| 2002/0152768 | A1 | 10/2002 | Loxley et al. |

FOREIGN PATENT DOCUMENTS

| EP | 0 241 384 | 10/1987 |
| WO | WO 02/47616 | 6/2002 |
| WO | WO 2005/103339 | 11/2005 |

*Primary Examiner* — Ling Xu
(74) *Attorney, Agent, or Firm* — Jacobson Holman PLLC

(57) ABSTRACT

A process for the preparation of a ceramic molded part from a suspension/dispersion with a solids content and a fluid content by depositing solids content at the periphery of a porous self-supporting support that is at least partially immersed in the suspension/dispersion and has the same shape as the molded part to be prepared, but with a reduced size, wherein:
  the solids content contains oxide-ceramic particles;
  the porous self-supporting support is detachably connected with a discharge in a zone that is not immersed in the suspension/dispersion;
  the suspension/dispersion is moved towards the porous self-supporting support by means of a positive pressure difference between a pressure prevailing in the suspension/dispersion and a pressure prevailing in the discharge;
wherein the fluid content of the suspension/dispersion enters in the porous self-supporting support with depositing solids content at the periphery of the porous self-supporting support.

27 Claims, 4 Drawing Sheets

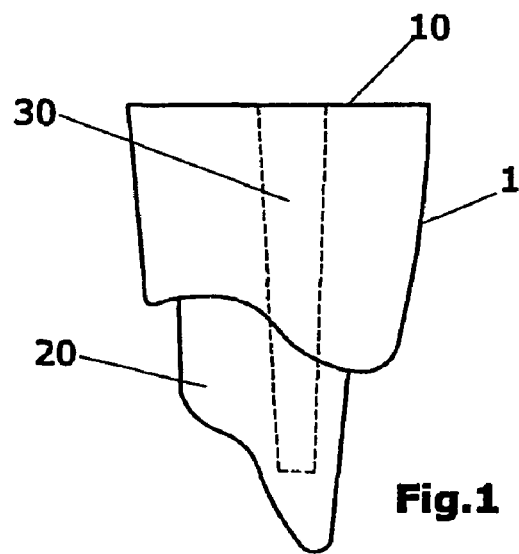
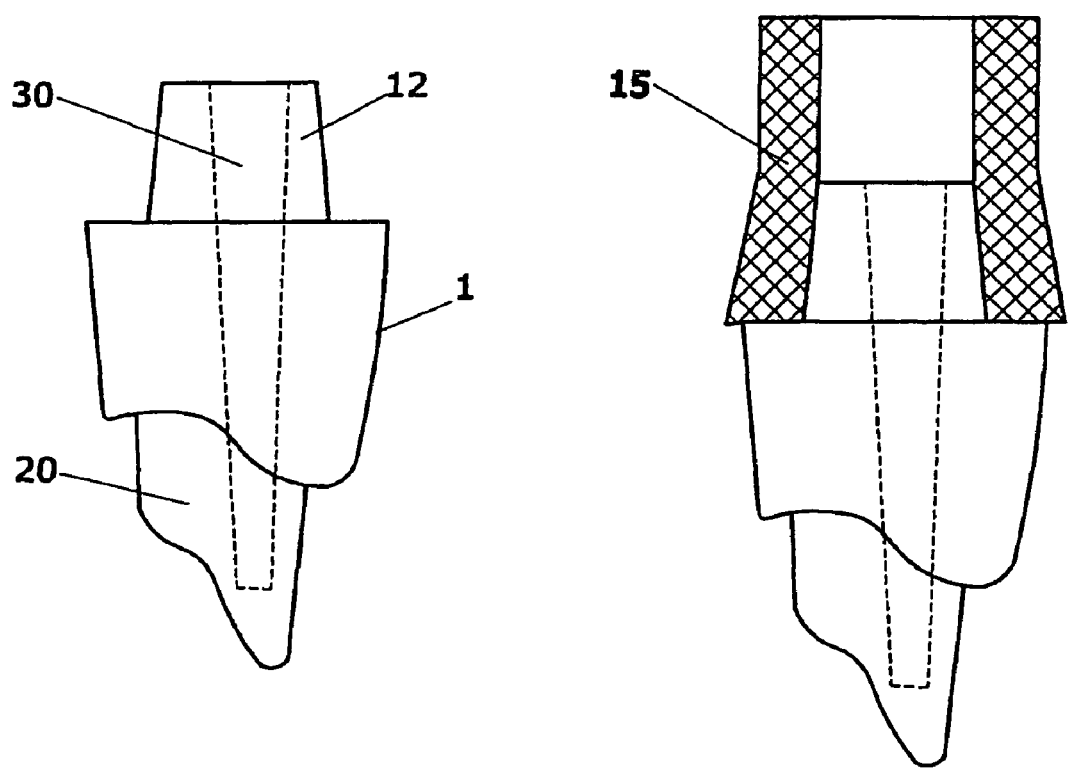

METHOD FOR THE PRODUCTION OF A CERAMIC MOLDED PART

This is a 371 of PCT/EP2007/060546 filed Oct. 4, 2007.

The present invention relates to a process for the preparation of a ceramic molded part from a suspension/dispersion with a solids content and a fluid content as well as a porous self-supporting support that can be used for the preparation of a ceramic molded part.

In the field of the preparation of dental prostheses, the slip technique developed by Sadoun has become established in recent years for high quality dental prostheses. The method is described in detail in EP-A-0 241 384. Although this technique makes high demands on the dental technician, it can be learned and then yields excellent results.

U.S. Pat. No. 4,155,964 discloses a technology for building dental-ceramic molded parts. In this method, a repulverized dental porcelain in a slurry is applied to a mold by immersing the mold into a slurry of the dental porcelain, which also contains a binder, and then dried on support by sucking off the liquid of the slurry in one embodiment. Another embodiment is realized by providing a porous impression material in a container and pressing the negative form of the composition to be impressed into such material, and filling the cavity formed with the slurry, followed by depositing it on the inner periphery of the impressed form either by centrifugation or by sucking off the solids in the slurry. A drawback of the latter variation is the fact that it is difficult to remove the produced molded part from the cavity and to forward it to further processing steps. The impression material is a relatively hard porous molding material that is not self-supporting, because it is provided within a container.

There is a need for a process in which the necessary slip construction is more independent of the skill of a dental technician.

The object of the invention is achieved by a process for the preparation of a ceramic molded part from a suspension/dispersion with a solids content and a fluid content by depositing solids content at the periphery of a porous self-supporting support that is at least partially immersed in the suspension/dispersion and has the same shape as the molded part to be prepared, but with a reduced size, wherein:
the solids content contains oxide-ceramic particles;
the porous self-supporting support is detachably connected with a discharge in a zone that is not immersed in the suspension/dispersion;
the suspension/dispersion is moved towards the porous self-supporting support by means of a positive pressure difference between a pressure prevailing in the suspension/dispersion and a pressure prevailing in the discharge;
wherein the fluid content of the suspension/dispersion enters in the porous self-supporting support with depositing solids content at the periphery of the porous self-supporting support.

BRIEF DESCRIPTION OF THE DRAWINGS

FIGS. 1, 2a, 2b, and 4 are views of alternative embodiments of a porous self-supporting support in accordance with the instant invention.

Figure 3A:
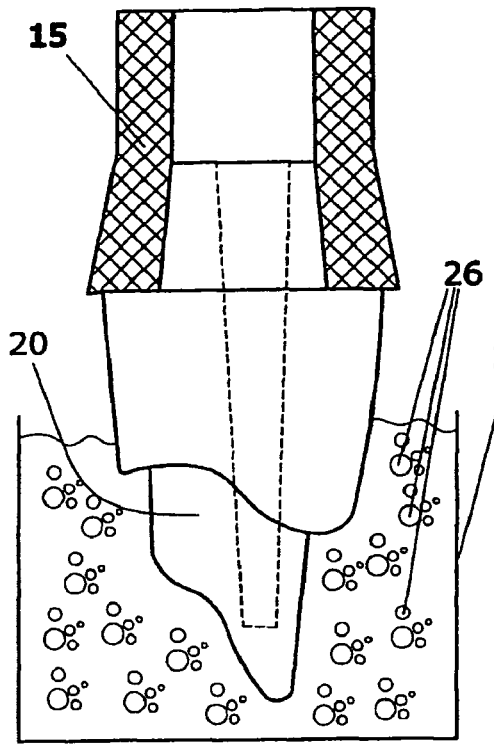
FIGS. 3a, 3b, 3c, and 3d schematically illustrate a course of the method in accordance with the instant invention.
Figure 3B:
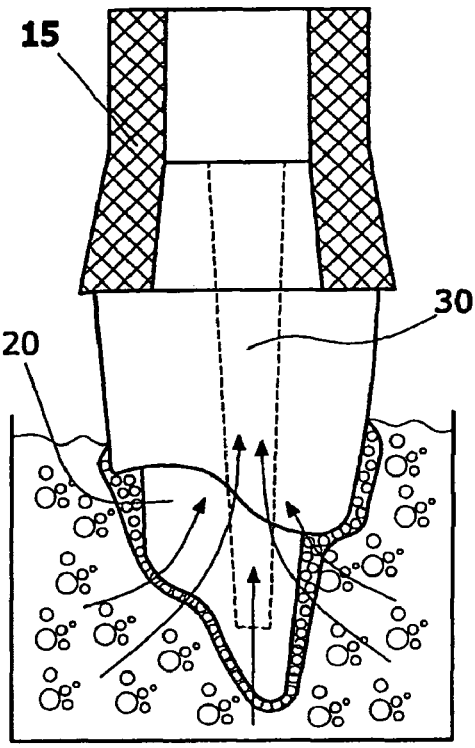
Figure 3C:
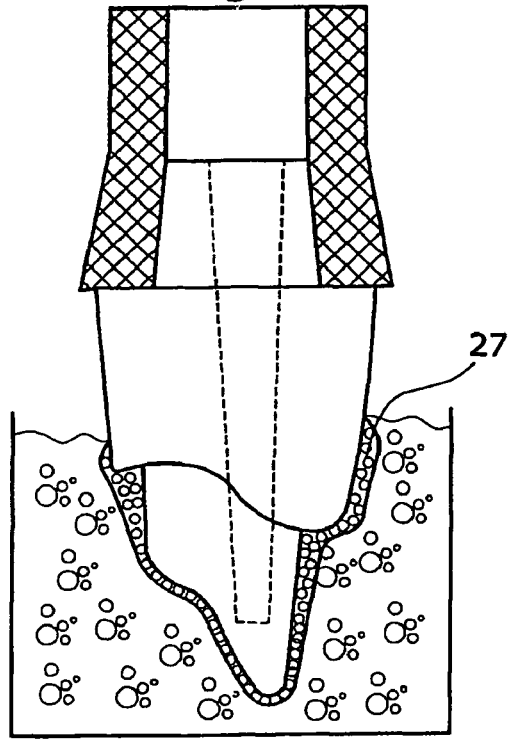
Figure 3D:
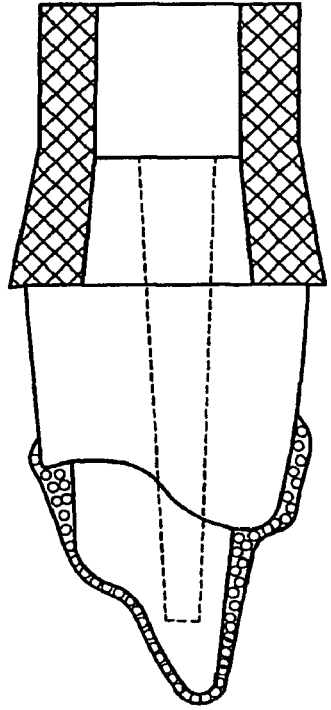

The process according to the invention enables a quick succession in the preparation of several differing molded parts, wherein the conventional slip technology by paintbrush application can be dispensed with. The technique of applying the slip with a paintbrush is tedious and needs some practice. According to the invention, the layer thickness of the molded parts can be advantageously adjusted reproducibly by selecting the duration of the reduced pressure. As compared to conventional slip technology in which the applicant needs experience in the handling of the ceramic slip, faults from non-uniform application are practically excluded. The risk of too long drying of individual manually applied slip layers with the resulting formation of an inhomogeneous structure (so-called onion shell effect) as well as the formation of pores are also reduced. Another advantage of the process according to the invention is based on the excellent fitting accuracy of the scaffolds prepared with the slip. The slip technology is employed, in particular, in the In-Ceram® technology of the Vita Zahnfabrik Henry Rauter GmbH & Co. KG and is also known among those skilled in the art due to the excellent service lives of the thus prepared dental restorations.

In particular, the ceramic molded part is a dental-ceramic molded part.

The porous self-supporting support that can be employed in the process according to the invention consists, for example, of gypsum, cured or other stump compositions known in dental technology, especially phosphate-bound powder mixtures, quartz and/or metal oxides.

The self-supporting porous support according to the invention is prepared, for example, by casting gypsum mixed with distilled water or other curable materials into a silicone impression of the master model. After the curable material has cured, which is after reaching the required curing expansion in the case of the In-Ceram special gypsum, the side not facing towards the suspension is ground flat, for example, with a gypsum trimmer, but a discharge may also be applied as set forth above. It is also possible to prepare the self-supporting porous support by grinding from a block of the curable material in question on the basis of CAD/CAM data by analogy with the grinding of a restoration of ceramic block material. With this preparation method, the setting of any magnification factors desired of the stump can be realized. Another possibility for preparing the self-supporting porous stump according to the invention is producing a magnified impression of the master model by means of a suitable expansion material for compensating the sintering shrinkage in the case of material to be sintered dense. This impression is cast with gypsum or similar materials to obtain an enlarged self-supporting porous stump.

It may be advantageous that the porous self-supporting support that can be employed in the process according to the invention has at least one zone that prevents the fluid content of the suspension/dispersion from entering.

In one embodiment of the process according to the invention, the porous self-supporting support can have a generally planar surface on a side not facing towards the suspension/dispersion. The generally planar surface may be connected with the discharge for convenience. It may be advantageous that the generally planar surface is provided with a flange.

In another embodiment, the generally planar surface is provided with a connecting element. As said connecting element, any elements by means of which two separate elements can be detachably connected may be used. In principle, in addition to mechanical connecting elements, chemical connecting elements may also be used. A typically mechanical connecting element is the above mentioned flange, for example, whereas adhesive bonding may be used, for example, as a chemical connecting element.

Another reasonable embodiment is obtained by the porous self-supporting support having at least one bore, especially a blind bore.

The suspension/dispersion to be employed in the process according to the invention is typically an oxide-ceramic suspension/dispersion for the field of dental-ceramic restorations. The oxide-ceramic suspension/dispersion may contain alumina, zirconia, magnesium aluminum oxide (spinel), yttria, ceria, silicates, zirconium silicate or combinations thereof.

The positive, pressure difference to be applied in the process according to the invention may be caused, for example, by an overpressure on the side of the porous self-supporting support facing towards the suspension/dispersion, and/or by a reduced pressure on the side of the porous self-supporting support facing away from the suspension/dispersion. In the case of a reduced pressure to be applied, it is applied, in particular, in the region of the discharge. In addition or exclusively, the reduced pressure may also be applied in the region of the bore. The pressure difference is suitably from 100 to 1000 mbar. If it appears necessary, the pressure difference may also deviate above or below the mentioned range.

For depositing very thick layers, a greater pressure difference may also be necessary. Accordingly, a stronger reduced pressure or overpressure would have to be applied even for a smaller pore size of the stump material. All in all, the material transport can be controlled through the pressure difference. The pressure differences suitable for the individual purposes can be determined by the skilled person simply by serial experiments.

Usually, a reduced pressure of lower than 500 mbar is applied.

In principle, the porosity of the porous self-supporting support can be formed by pores that are not greater than 20 micrometers. Typically, the size of the pores is within a range of from 1 nm to 10 µm (measured by means of mercury porosimetry).

It is also well known to the skilled person to deviate from the pore sizes mentioned here. For example, materials having a smaller pore size may also be used for the deposition according to the invention in principle. However, if materials having larger pores should be used, a layer of a material with a smaller pore size could be advantageously applied in order to prevent the ceramic particles from the suspension or dispersion from entering the porous self-supporting stump material.

In another embodiment of the invention, after depositing a solids content on the periphery in a layer having a predetermined layer thickness, the porous self-supporting support can be immersed in a second suspension/dispersion, so that the previously formed layer is at least partially immersed in the second suspension/dispersion, and the process steps described are repeated. Of course, it is possible optionally to repeat further immersion processes in order to build up several layers.

In one embodiment of the process according to the invention, the porous self-supporting support can be withdrawn after one or more layers have been built, wherein a pressure difference is maintained in order to achieve extensive predrying.

It is up to the skilled person to choose if the ceramic molded part obtained is provided with a higher strength by an aftertreatment. According to the invention, sintering of the ceramic molded part and/or infiltration with inorganic or organic materials may be used as aftertreatment.

The sintering is performed, in particular, at temperatures of from 600° C. to 1600° C. As organic materials for infiltration, polymerizable organic compounds may be used, in particular. Typically, compounds having at least one ethylenically unsaturated bond are used. In particular, urethane dimethacrylate (UDMA) and/or triethylene glycol dimethacrylate (TEGDMA) lend themselves for this purpose.

The inorganic materials include infiltration glasses, especially lanthanum borate glasses. Such infiltration glasses are employed in the long known slip technology. The disclosure of EP-A-0 241 384 is included herewith by reference.

The process according to the invention is further illustrated by FIGS. 1 to 4.

The present invention also relates to a porous self-supporting support 1 with a base 10 and a superstructure 20, which has a shape to be coated with a solid, and a bore 30, which runs through the base 10 and the superstructure 20 and is designed as a blind bore (FIG. 1). As shown in FIG. 2a, a means 12 may be provided on the base 10 for connecting a discharge means 15. The discharge means may be connected to a pump for producing a reduced pressure (FIG. 2b). The discharge means may be a pressure hose, for example.

FIGS. 3a to 3d schematically show the course of the method according to the invention. In FIG. 3a, the device as shown in FIG. 2b is immersed in a container 25 that contains the suspension/dispersion employed for building the molded part. The particles 26 of the suspension/dispersion are suctioned after a reduced pressure has been applied to the porous self-supporting support according to the invention, and are deposited at the periphery of superstructure 20. The arrows represent the direction of the pressure gradient towards lower pressures. After the desired layer thickness of slip material 27 has been reached at the periphery of the superstructure and the porous self-supporting support, the reduced pressure is turned off, and the assembly is removed from the container. Then, after the discharge means has been removed, the assembly shown in FIG. 3d can be further processed in a per se known manner. The height of the slip layer can be controlled by immersing the porous self-supporting support into the suspension/dispersion.

Figure 4:
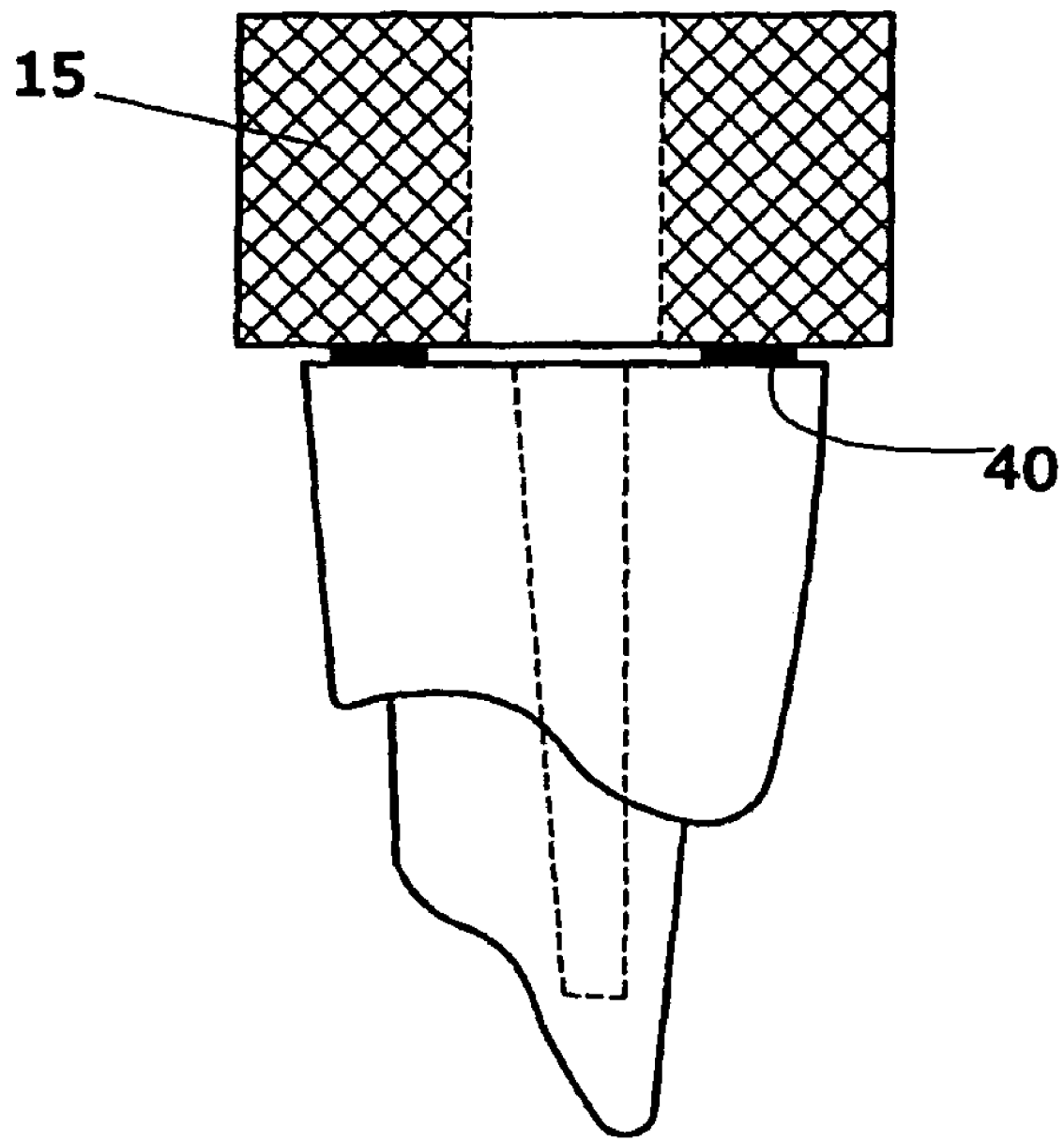

FIG. 4 shows another embodiment of the superstructure that can be employed in the process according to the invention.

The self-supporting porous support 1 can be attached to the discharge means 15 with a fixing material 40. This can be simply effected, in particular, with the following means:
- double-sided adhesive tape in ring form (such as reinforcement washers), optionally in a thickness of material that levels out the unevenness of the substrate;
- an adhesive kneadable composition that is applied in ring form around the bore 30 and attached by manually pressing against the discharge means 15.
- what is also suitable is a magnetic adhesive tape that is connected with a magnetic discharge means 15;
- or the use of a reusable magnetic plate that is attached to the porous support 1 by means of one of the first two examples and then hanged to the magnetic discharge means 15.

After the deposition process, the gypsum stump with the fixing material is to be preferably detachable from the discharge means 15 without a residue in order that the next gypsum stump can be hanged for deposition. These mentioned embodiments are alternatives to attaching the porous self-supporting support 1 by means of the silicone hose to the discharge means 15.

The porous self-supporting support according to the invention is excellently suitable for use in the process according to the invention.

Figure 5:
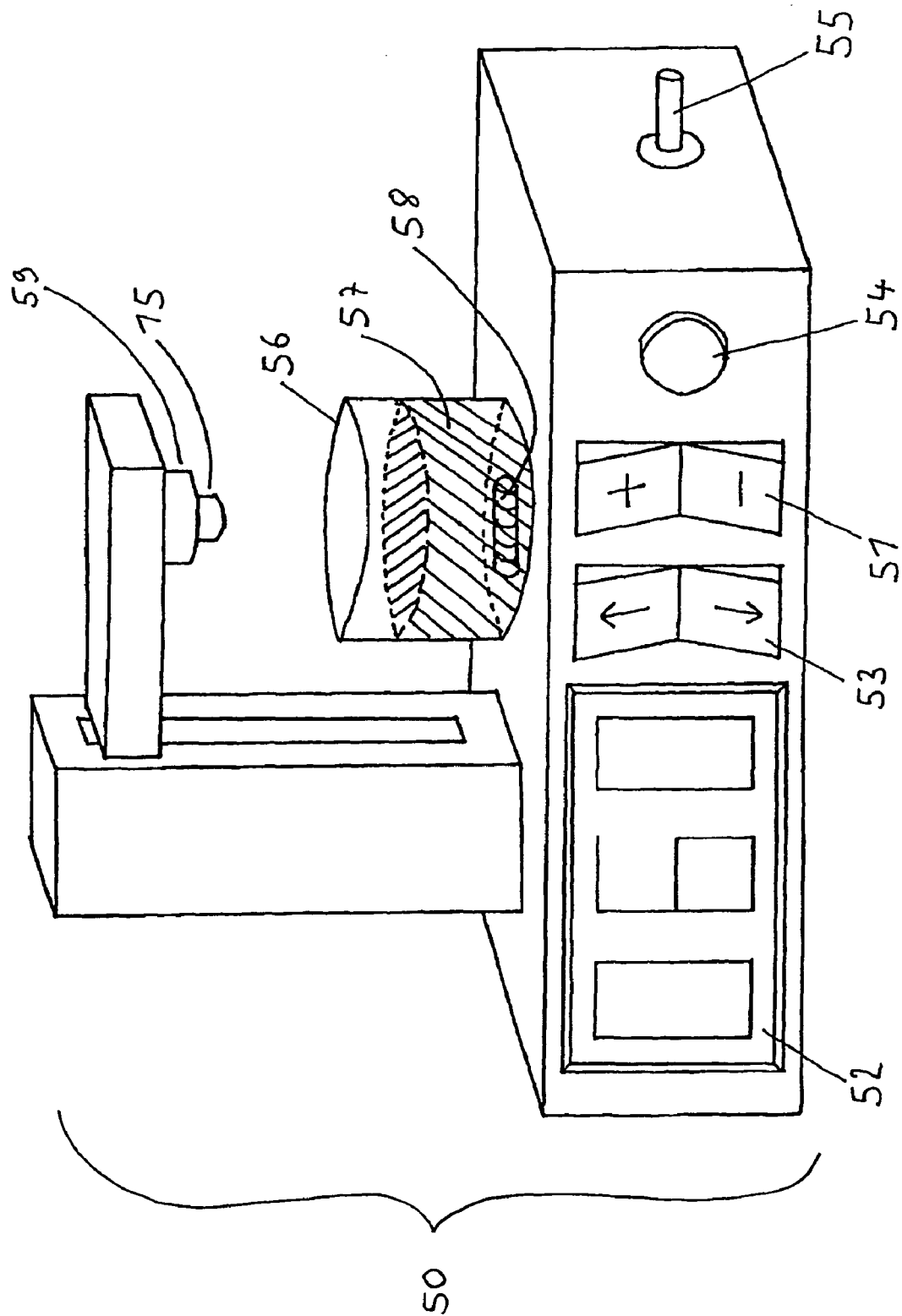
FIG. 5 details, in perspective, a device embodiment in accordance with the instant invention.

FIG. 5 shows in detail a device 50 according to a particular embodiment of the invention.

51: rocker switch for setting the suction time
52: suction time display
53: rocker switch for vertically moving the holder up and down
54: starting button for turning the process on (vacuum starts, and after lapse of the preset time, the vacuum turns off automatically, and the holder is moved up.)
55: port for vacuum or compressed air
56: slip container
57: slip (suspension/dispersion)
58: magnetic stirring bar
15: discharge means
59: vertically moveable holder with discharge means The invention will be further illustrated by the following Example.

The process according to the invention is based on slip deposition on the surface of a porous gypsum stump provided with a bore. The gypsum stump is ground flat at the bottom side thereof and dimensioned to enable a flexible tube, especially silicone tube, to be pulled over it (or connected with it) as an adapter in a vacuum-tight manner. The gypsum stump provided with the flexible tube is pushed onto a flange or connected with an adapter that is attached to a moveable holder for receiving the gypsum stump. The holder is preferably moveable by motor and can be inserted into the container provided below that contains the slip. The slip is agitated by means of a stirrer, for example, a magnetic stirring motor with a magnetic stirring bar, in order to prevent sedimentation of the slip. A vacuum line is provided next to the holder and connected with a device for producing a reduced pressure, for example, a pump. Thereafter, the gypsum stump is inserted into the slip manually or by automatic control until the preparation boundary is completely covered. After the gypsum stump has been inserted into the slip, a reduced pressure is applied. During the deposition process, the slip is not stirred. After the predetermined time, the pressures are equalized, which is done while the gypsum stump with the deposited material is still within the slip. Thereafter, the holder can be moved up again to the initial position. The gypsum stump with the cap deposited thereon can be removed from the flange or adapter and further processed. Thereafter, the device is available for further processing.

Typically, the layer thickness of the slip can be varied by varying the reduced pressure time. Thus, for example, a suction time of about 20 s to 60 s, especially about 40 s, can be observed when a 0.7 mm thick front tooth cap is produced, and a suction time of from 30 to 90 s, especially about 60 s, can be observed when an equally thick side tooth cap is produced.

The invention claimed is:

1. A process for the preparation of a ceramic molded part from a suspension/dispersion with a solids content and a fluid content by depositing solids content at the periphery of a porous self-supporting support that is at least partially immersed in the suspension/dispersion and has the same shape as the molded part to be prepared, but with a reduced size, wherein:
   the solids content contains oxide-ceramic particles;
   the porous self-supporting support is detachably connected with a discharge in a zone that is not immersed in the suspension/dispersion;
   the suspension/dispersion is moved towards the porous self-supporting support by means of a positive pressure difference between a pressure prevailing in the suspension/dispersion and a pressure prevailing in the discharge;
   wherein the fluid content of the suspension/dispersion enters in the porous self-supporting support with depositing solids content at the periphery of the porous self-supporting support.

2. The process according to claim 1, wherein said ceramic molded part is a dental ceramic molded part.

3. The process according to claim 1, wherein said porous self-supporting support consists of cured gypsum, stump compositions, quartz, metal oxides.

4. The process according to claim 1, wherein said porous self-supporting support has at least one zone that prevents the fluid content of the suspension/dispersion from entering.

5. The process according to claim 1, wherein said porous self-supporting support has a generally planar surface on a side not facing towards the suspension/dispersion.

6. The process according to claim 5, wherein said generally planar surface is connected with said discharge.

7. The process according to claim 6, wherein said generally planar surface is provided with a flange.

8. The process according to claim 6, wherein said generally planar surface is provided with a connecting element.

9. The process according to claim 8, wherein said connecting element is represented by adhesive bonding.

10. The process according to claim 1, wherein said porous self-supporting support has at least one bore.

11. The process according to claim 10, wherein said bore is a blind bore.

12. The process according to claim 10, wherein said oxide-ceramic suspension/dispersion contains alumina, zirconia, magnesium aluminum oxide (spinel), yttria, ceria, silicates, zirconium silicate or combinations thereof.

13. The process according to claim 1, wherein said suspension/dispersion is an oxide-ceramic suspension/dispersion.

14. The process according to claim 1, wherein said positive pressure difference is caused by an overpressure on the side of the porous self-supporting support facing towards the suspension/dispersion, and/or by a reduced pressure on the side of the porous self-supporting sup-port facing away from the suspension/dispersion.

15. The process according to claim 14, wherein said reduced pressure is applied in the region of the discharge.

16. The process according to claim 15, wherein said reduced pressure is also applied in the region of the bore.

17. The process according to claim 14, wherein said pressure difference is from 100 to 1000 mbar.

18. The process according to claim 14, wherein a reduced pressure of less than 500 mbar is applied.

19. The process according to claim 1, wherein the porosity of the porous self-supporting support is from 1 nm to 10 μm as measured by means of mercury porosimetry.

20. The process according to claim 1, wherein after depositing a solids content on the periphery in a layer having a predetermined layer thickness, the porous support is immersed in a second suspension/dispersion, so that the previously formed layer is at least partially immersed in the second suspension/dispersion, and the process of claim 1 is repeated, and optionally further immersion processes are repeated to build up several layers.

21. The process according to claim 20, wherein said after-treatment comprises the sintering of the ceramic molded part and/or infiltration with inorganic or organic materials.

22. The process according to claim 21, wherein said organic materials for infiltration are polymerizable organic compounds, especially urethane di-methacrylate (UDMA)

and triethylene glycol dimethacrylate (TEGDMA), and said inorganic materials are infiltration glasses, especially lanthanum borate glasses.

23. The process according to claim 1, wherein the pressure difference is maintained after the porous self-supporting support with one or more layers is withdrawn, to achieve extensive predrying.

24. The process according to claim 23, wherein said sintering is performed at temperatures of from 600° C. to 1600° C.

25. The process according to claim 1, wherein the ceramic molded part obtained is provided with a higher strength by an aftertreatment.

26. A porous self-supporting support (1) with a base (10) and a superstructure (20), which has a shape to be coated with a solid, and a bore (30) which runs through the base (10) and the superstructure (20) and is designed as a blind bore, wherein a discharge means (15) for discharging fluid contents of a suspension/dispersion consisting of a solids content and a fluid content is provided in a region of the base (10).

27. A molded part comprising the porous self-supporting support of claim 26 having a solid coating thereon, wherein the molded part has a shape corresponding to the shape of the porous self-supporting support.

* * * * *